United States Patent
Bechmann

(10) Patent No.: US 6,752,028 B2
(45) Date of Patent: Jun. 22, 2004

(54) LOAD MONITORING TEST DEVICE FOR A PATIENT'S FOOT

(76) Inventor: Peter Bechmann, Malensteinstrasse 2, Oberammergau (DE)

( * ) Notice: Subject to any disclaimer, the term of this patent is extended or adjusted under 35 U.S.C. 154(b) by 179 days.

(21) Appl. No.: 10/026,323

(22) Filed: Dec. 18, 2001

(65) Prior Publication Data

US 2002/0093428 A1 Jul. 18, 2002

(30) Foreign Application Priority Data

Dec. 19, 2000 (DE) .................................. 200 21 422 U

(51) Int. Cl.[7] .................................................. G01L 1/26
(52) U.S. Cl. .................................................. 73/862.391
(58) Field of Search ................. 73/862.041, 862.043, 73/862.046, 862.391

(56) References Cited

U.S. PATENT DOCUMENTS

| 3,702,999 | A | * | 11/1972 | Gradisar | 340/573.1 |
| 3,791,375 | A | * | 2/1974 | Pfeiffer | 600/592 |
| 4,703,445 | A | * | 10/1987 | Dassler | 702/160 |
| 5,112,560 | A | * | 5/1992 | Moumdjian | 264/516 |
| 5,169,364 | A | * | 12/1992 | Donaldson | 482/105 |
| 5,282,288 | A | * | 2/1994 | Henson | 12/142 P |
| 6,031,463 | A |  | 2/2000 | Bechmann |  |
| 6,351,205 | B1 | * | 2/2002 | Armstrong | 338/114 |

FOREIGN PATENT DOCUMENTS

| DE | 4100834 A1 | 7/1992 |
| DE | 19625474 A1 | 1/1998 |

* cited by examiner

*Primary Examiner*—Max Noori
(74) *Attorney, Agent, or Firm*—Ostrolenk, Faber, Gerb & Soffen, LLP

(57) ABSTRACT

A test device for monitoring a predetermined pressure load on a patient's foot as exerted by the body weight of the patient during walking has a pressure sensor which is designed as a circular, ring-shaped, curved washer having a snap portion in the form of a conically shaped elevation that can be snapped-over from a rest position into an active monitoring position when a predetermined pressure load is sensed. This the snapping action is accompanied by an audible signal as well as by a sensitive sensing signal acting bodily against the heel of the patient's foot under which the test device is placed.

19 Claims, 4 Drawing Sheets

LOAD MONITORING TEST DEVICE FOR A PATIENT'S FOOT

BACKGROUND OF THE INVENTION

This invention relates to a test device for monitoring a predetermined pressure load on a patient's foot as exerted by a body rate of the patient during walking.

Test devices of the above kind are used for warning a patient in those cases were due to a fracture of a leg or any other orthopedic surgery operations the factual load on the patient's leg as related to the patient's body weight must be limited. As regards the particular therapy of more or less complicated leg fractures as well as orthopedic operations for example on a patient's hip an initial load on the patient's foot of only about 20 kg is more generally considered as an allowable maximum limit when the patient will start with his first attempts to walk after a respective operation. Such a lowermost load which of course is only a fraction of the patient's body weight will then subsequently be increased stepwise whereby only with a corresponding number of steps of increasingly higher pressure loads on the patient's foot a correct heeling or recovery of the operated leg or hip will be secured. It is therefore most essential to continuously monitor the pressure load on the patient's foot as exerted during walking by any suitable test device which should be easy in handling by the patient.

A prior art device as described in German Patent Publication DE 41 00 834 A1 comprises an elastic pressure chamber filled with air under atmospheric pressure and provided for being placed under the patient's foot. The pressure chamber forms a pressure sensor which is incorporated into a shoe sole and interconnected with an analog indicating instrument via a flexible line whereby the indicating instrument comprises an electronic measurement equipment and indicator lamps for indicating a correct or otherwise incorrect pressure load on the patient's foot.

A similar test device is described in U.S. Pat. No. 6,031, 463 which comprises as a pressure sensor a resilient foot pad filled with a fluid and connected via a fluid line to a pressure responsive means that is adapted to actuate a signalling means at a predetermined pressure of the liquid in the resilient foot pad under a predetermined load on the patient's foot. The signalling means comprises a so-called click spring which is arranged for supplying an audible click noises when actuated by the pressure responsive means, the click noise being obtained by a translent deformation of a deformable bulge of the click spring whenever the click spring is leaving a respective rest position and is again returning to the same. The click spring is preferably arranged within a box serving as a resonance body for amplifying its click noise, the click spring being preferably biased against a lever which is in operational contact with the pressure responsive means and adapted to actuate the click spring for supplying its click noise.

BRIEF SUMMARY OF THE INVENTION

The present invention deals with the object of providing a less expensive and at the same time more reliable load monitoring test device for a patient's foot of the kind as above referred. The test device when being used should moreover be adapted for securing a therapy as effective as possible by strictly complying with a series of multiple steps as prescribed by the patient's physician subsequent to an operation for again obtaining a healthy leg or hip portion which has undergone an orthopedic operation.

A test device for monitoring a predetermined pressure load comprises in accordance with the present invention a pressure sensor which is to be placed under the heel to the patient's foot for monitoring a predetermined pressure load. In accordance with a specific aspect under the present invention this pressure sensor is a circular, ring-shaped, curved washer which has a snap portion that is adapted for being snapped-over from a rest position under a predetermined pressure load and snapped into an active monitoring position whereby this snapping action is accompanied by an audible signal and further by a sensitive sensing signal acting bodily against the heel of the patient's foot. Upon relief of the predetermined pressure load the snap portion of the curved washer will again be returned into its rest position. In accordance with a preferred embodiment of the test device according to the present invention the snap portion of the curved washer comprises a conically shaped elevation which surrounds the central opening of the curved washer and which is adapted to snap a respectively adjacent portion of the washer into its active monitoring position.

In accordance with a further preferred aspect of the present invention the circular, ring-shaped, curved washer is arranged between first and second pressure plates are designed as shoe inserts whereby a first pressure plate is used as a heel support for the patient's foot and is preferably provided with an elevated portion which is in contact with the snap portion of the curved washer. The first and second pressure plates should both be designed as dishes in the form of a rest for the patient's heel and should preferably be interlinked by a common pivot means for being relatively movable with respect to each other to thereby easily allow the arrangement of the curved washer between the two plates as well as its replacement against a new washer that will secure a monitoring of a different predetermined pressure load on the patiant's foot.

A test device in accordance with the present invention is accordingly most distinguished over comparable devices of the prior art in the feature of providing not only an audible signal when a predetermined pressure load is reached but in providing also a sensitive sensing signal that bodily acts against the heel of the patient's foot. Such a sensitive sensing signal will definitely be felt even by elder people for then immediately reacting with a relief of the pressure load on the foot of the leg that is under recovery. The test device may also be produced at low costs and may be maintained safely over a long period due to its absence of separate fluid or other signal lines.

DETAILED DESCRIPTION

A test device 1 in accordance with the present invention is designed for being placed under the heel of a patient's foot for monitoring a predetermined pressure load as exerted by the body weight of the patient during walking. The device may be fixed on the patient's leg by means of a loop band 2 if necessary.

Figure 4:
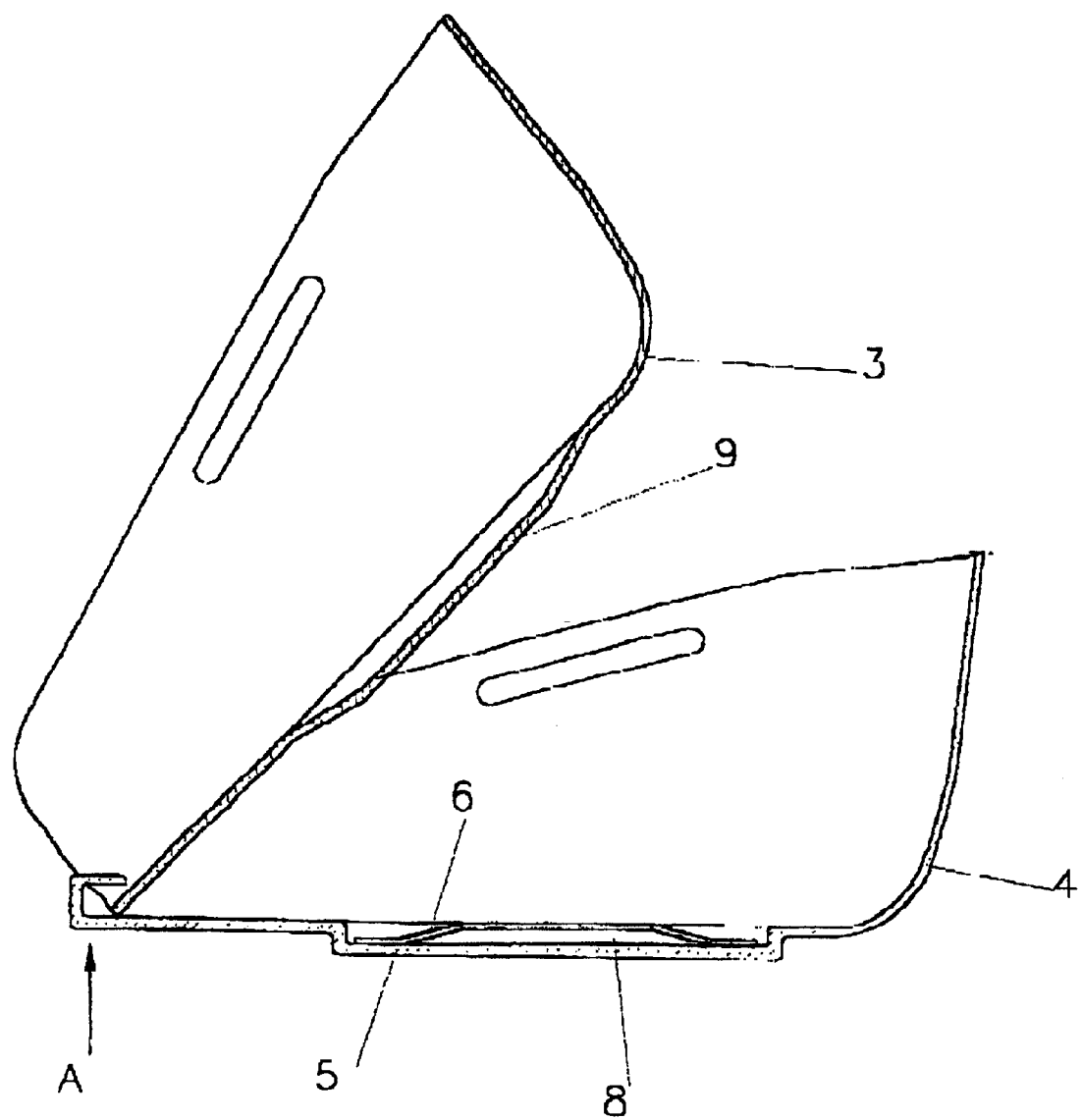
FIG. 4 is a side view of the test device in its opened position.

As shown in FIG. 4 the test device 1 comprises two pressure plates 3 and 4 which are designed as dishes serving as a rest for the patient's heel. These two pressure plates 3, 4 are interlinked by a common pivot means as shown by the arrow A for being relatively movable with respect to each other. When the two pressure plates 3, 4 are opened as shown in FIG. 4 this will allow an arrangement of a circular ring-shaped, curved washer 5 on the bottom of the one pressure plate 4. The curved washer 5 has a conically shaped elevation 6 which surrounds a central opening 7 of the washer whereby this particular elevation 6 essentially forms a pressure sensor of the test device for sensing the pressure load on a patient's foot.

The curved washer 5 is arranged within a recess 8 of the one pressure plate 4 in such a manner that its conically shaped elevation 6 is directed upwardly. The arrangement of the curved washer 5 within the recess 8 of the pressure plate 4 is such that when the other pressure plate 3 is turned downwardly around the common pivot means A a correspondingly elevated portion 9 on the pressure plate 3 will come into contact with the conically shaped elevation 6 of the curved washer 5.

Figure 3:
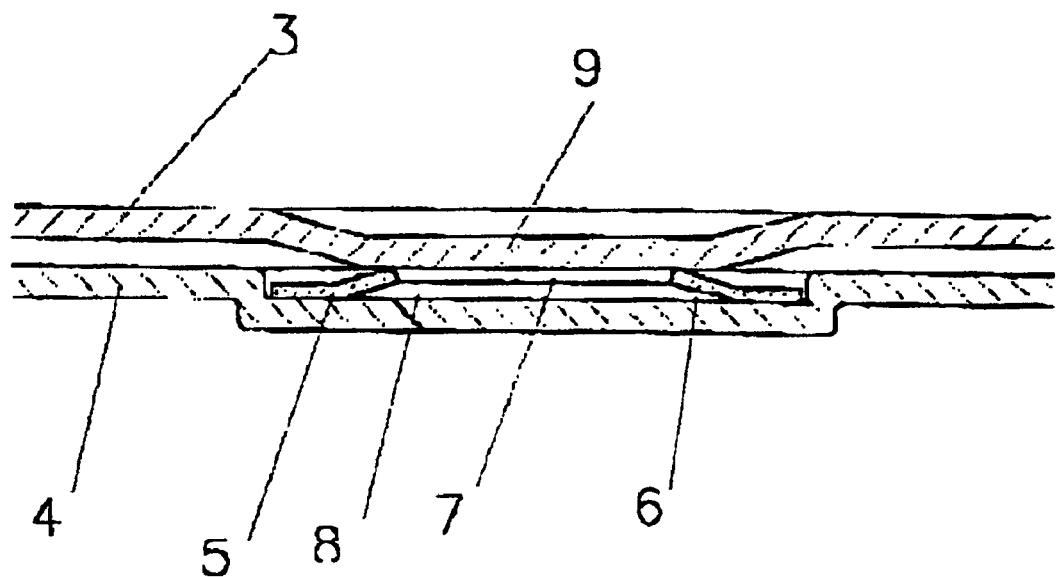
FIG. 3 is a schematic view showing the two functional positions of the snap portion of the curved washed.
Figure 3:
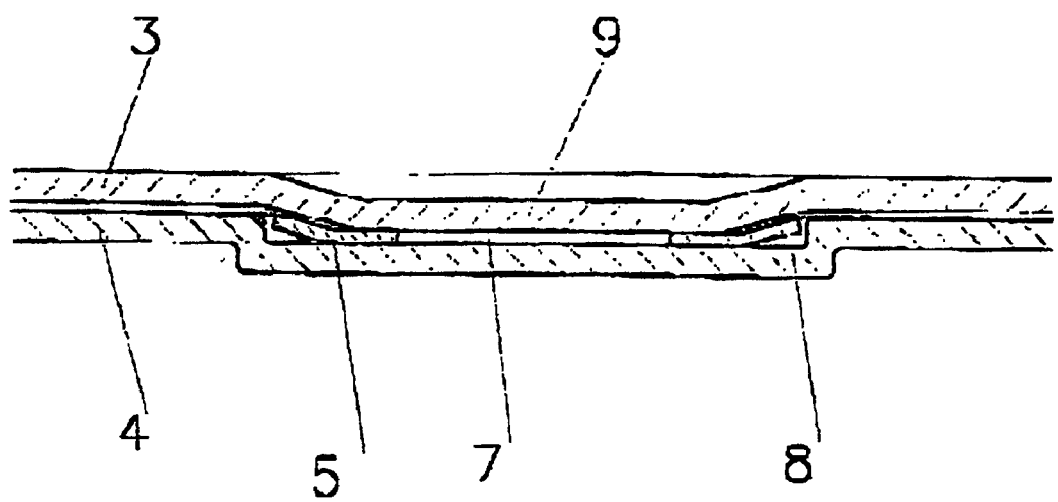

As diagrammatically shown in FIG. 3 it should be understood that when the two pressure plates 3, 4 are closed with an arrangement of the curved washer 5 within the recess 8 of the one pressure plate 4 the conically shaped elevation 6 of the washer 5 will maintain a rest position as long as no pressure load will be exerted on the washer via the pressure plate 3 that is arranged on top of the pressure plate 4. The relative position of the two pressure plates 3 and 4 at the location of the conically shaped elevation 6 of the curved washer 5 and of the mutually aligned elevated portion 9 of the pressure plate 3 as shown by the upper sectional view in FIG. 3 will thereby be maintained by the spring characteristic of the curved washer 5 as concentrated in the conically shaped elevation 6 which surrounds the central opening 7 of the curved washer.

Figure 1:
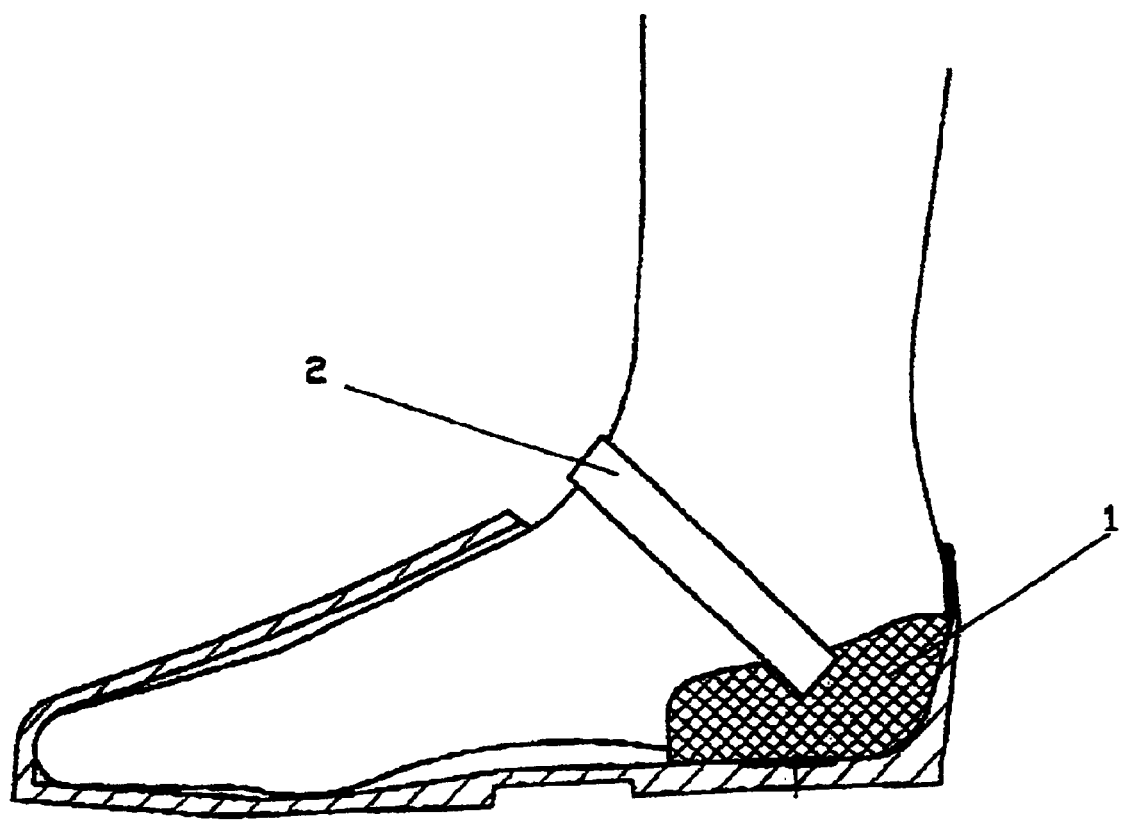
FIG. 1 is a side view of a patient's foot carrying a test device in accordance with the present invention.
Figure 2:
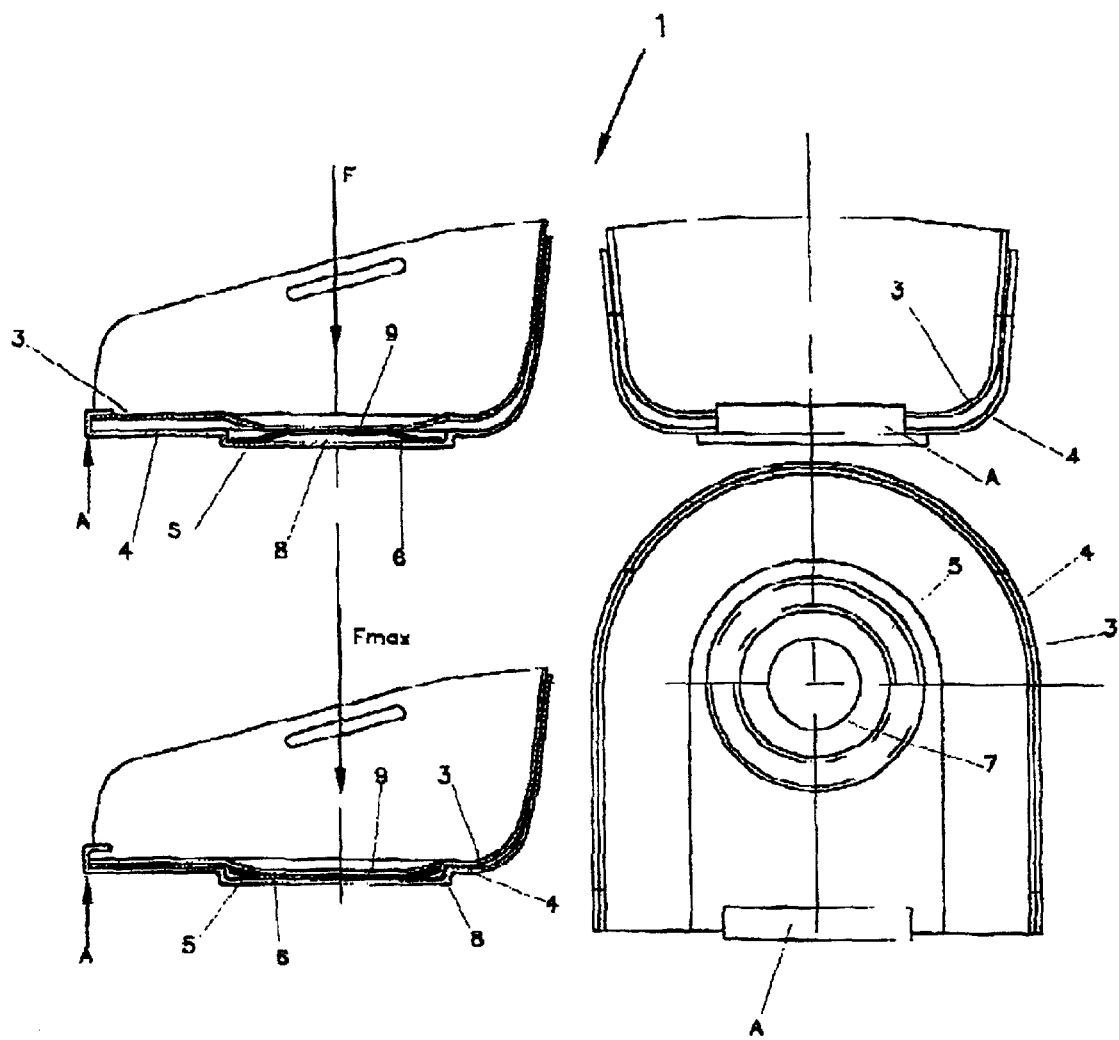
FIG. 2 shows different views of the test device whereby the curved washer which is used as a pressure sensor is shown with its snap portion in a rest position free of any pressure load and in a snapped-over active monitoring position.

As further shown in FIG. 2 the conically shaped elevation 6 of the curved washer 5 will maintain its elevated rest position as long as the downwardly directed force F as applied via the elevated portion 9 of the pressure plate 3 against this conically shaped elevation 6 will be lower than a predetermined pressure load on the patient's foot as exerted by the body weight of the patient. As soon as this predetermined pressure load reaches a limit at a force $f_{max}$ which is higher than the spring characteristic or hardness of the conically shaped elevation 6 of the curved washer 5 the conically shaped elevation will then snap-over into an active monitoring position as shown with the lower sectional view in FIG. 2. This snapping action will be tripped by the elevated portion 9 of the upper pressure plate 3 and will be accompanied by an audible signal. This audible signal is substantially obtained from the ring-shaped portion of the curved washer 5 which surrounds its conically shaped elevation 6 and which with the deformation of the same will be snapped upwardly so that not only an audible signal will thereby be obtained but also a sensitive sensing signal which then will bodily act against the heel of the patient's foot. Both signals which therefore monitor the existence of a predetermined pressure load on the patient's foot will therefore commonly signalise a necessary relief of the pressure load which when exercised by the patient will lead to a snapping of the conically shaped elevation 6 of the curved washer 5 back to its rest position under the action of its spring characteristic.

Any higher than an initial pressure load of for example 20 kg which is to be monitored by the test device may be obtained by a replacement of the curved washer by another curved washer having a correspondingly higher spring characteristic or hardness. Instead of providing curved washers with correspondingly different spring characteristics corresponding to different steps of predetermined pressure loads there could also be used curved washers having all the same spring characteristic or hardness so that with a multiple arrangement of such curved washers a corresponding multiplicity of basic predetermined pressure loads could be planned. In both cases when using different colours for identifying different spring characteristics this would assist a proper use of the test device under the control as prescribed by the physician supervising the curing period after an operation of a fractured leg or after any other orthopedic surgery operation.

What is claimed is:

1. A test device for monitoring predetermined pressure load on a patient's foot as exerted by a body weight of the patient during walking, comprising:

a pressure sensor for being placed under the heel of the patient's foot for monitoring a predetermined pressure load;

the pressure sensor comprising a circular, ring-shaped, curved washer having a snap portion which is adapted for being snapped-over from a rest position under a predetermined pressure load of the patient's foot and snapped into an active monitoring position whereby the snapping action is accompanied by an audible signal and further by a sensitive sensing signal acting bodily against the heel of the patient's foot, the snap portion of the curved washer being returned again into its rest position upon relief of the predetermined pressure load in which the snap portion of the curved washer comprises a conically shaped elevation which surrounds a central opening of the curved washer and is adapted to snap an adjacent edge portion of the curved washer into its active monitoring position.

2. The test device of claim 1, in which the curved washer is arranged between first and second pressure plates that are designed as shoe inserts whereby a first pressure plate is used as a heel support for the patient's foot.

3. The test device of claim 2, in which said first pressure plate which is used as a heel support of the patient's foot is provided with an elevated portion adapted for coming into contact with the snap portion of the curved washer.

4. The test device of claim 2, in which the first and second pressure plates are designed substantially as dishes in the form of a rest for the patient's heel.

5. A test device for monitoring a predetermined pressure load on a patient's foot as exerted by a body weight of the patient during walking, comprising:

a pressure sensor for being placed under the heel of the patient's foot for monitoring a predetermined pressure load;

the pressure sensor comprising a circular, ring-shaped, curved washer having a snap portion which is adapted for being snapped-over from a rest position under a predetermined pressure load of the patient's foot and snapped into an active monitoring position whereby the snapping action is accompanied by an audible signal and further by a sensitive sensing signal acting bodily against the heel of the patient's foot, the snap portion of the curved washer being returned again into its rest position upon relief of the predetermined pressure load;

in which the snap portion of the curved washer comprises a conically shaped elevation which surrounds a central opening of the curved washer and is adapted to snap an adjacent edge portion of the curved washer into its active monitoring position;

in which the curved washer is arranged between first and second pressure plates that are designed as shoe inserts whereby a first pressure plate is used as a heel support for the patient's foot; and in which the curved washer is arranged within a recess of the second pressure plate, the recess being aligned with an elevated portion of the first pressure plate and being provided for limiting a snapped-over monitoring position of the snap portion of the curved washer.

6. The test device of claim 5, in which said elevated portion of said first pressure plate is disposed for coming into contact with the snap portion of the curved washer.

7. The test device of claim 5, in which the first and second pressure plates are designed substantially as dishes in the form of a rest for the patient's heel.

8. A test device for monitoring a predetermined pressure load on a patient's foot as exerted by a body weight of the patient during walking, comprising:

a pressure sensor for being placed under the heel of the patient's foot for monitoring a predetermined pressure load;

the pressure sensor comprising a circular, ring-shaped, curved washer having a snap portion which is adapted for being snapped-over from a rest position under a predetermined pressure load of the patient's foot and snapped into an active monitoring position whereby the snapping action is accompanied by an audible signal and further by a sensitive sensing signal acting bodily against the heel of the patient's foot, the snap portion of the curved washer being returned again into its rest position upon relief of the predetermined pressure load;

in which the snap portion of the curved washer comprises a conically shaped elevation which surrounds a central opening of the curved washer and is adapted to snap an adjacent edge portion of the curved washer into its active monitoring position;

in which the curved washer is arranged between first and second pressure plates that are designed as shoe inserts whereby a first pressure plate is used as a heel support for the patient's foot; and in which the first and second pressure plates are interlinked by a common pivot for being relatively movable with respect to each other.

9. The test device of claim 8 in which the common pivot is provided in such a manner as to allow a positioning of the curved washer between the first and second pressure plates when adjusted into a relatively opened arrangement.

10. A test device for monitoring a predetermined pressure load on a patient's foot as exerted by a body weight of the patient during walking, comprising:

a pressure sensor which is to be placed under the heel of the patient's foot for monitoring a predetermined pressure load;

the pressure sensor comprising a circular, ring-shaped, curved washer having a snap portion which is formed with a conically shaped elevation adapted for being snapped-over from a rest position into an active monitoring position under a predetermined pressure load of the patient's foot whereby the snapping action of the snap portion is accompanied by an audible signal and further also by a sensitive sensing signal acting bodily against the heel of the patient's foot, the conically shaped elevation surrounding a central opening of the curved washer and being adapted to snap-over an adjacent edge portion of the curved washer into said active monitoring position and to turn it back again into its rest position on a relief of the predetermined pressure load.

11. The test device of claim 10, in which the curved washer is arranged between first and second pressure plates that are designed as shoe inserts and cooperatively used for snapping-over the conically shaped elevation under a predetermined pressure load as applied against a first pressure plate of said first and second pressure plates and used as a heel support for the patient's foot.

12. The test device of claim 11 in which said first pressure plate is provided with a downwardly oriented elevated portion adapted for coming into contact with the conically shaped elevation of the curved washer which is positioned underneath the first pressure plate.

13. The test device of claim 12 in which the curved washer is arranged within a recess of the second pressure plate of said first and second pressure plates, the recess being aligned with the elevated portion of the first pressure plate and being provided for limiting the active monitoring position of the snap portion of the curved washer.

14. The test device of claim 11 in which said first and second pressure plates are designed substantially as dishes in the form of a rest for the patient's heel.

15. The test device of claim 11 in which the curved washer is arranged within a recess of the second pressure plate of said first and second pressure plates, the recess being aligned with the elevated portion of the first pressure plate and being provided for limiting the active monitoring position of the snap portion of the curved washer.

16. The test device of claim 11 in which said first and second pressure plates are interlinked by a common pivot for being movable with respect to each other between a relatively opened and a relatively closed mutual positioning.

17. The test device of claim 16 in which the common pivot is provided in such a manner as to allow a positioning of the curved washer between the first and second pressure plates when being in the mutually opened position.

18. The test device of claim 10 in which distinct predetermined pressure loads are obtained with correspondingly distinct spring characteristics of a multiple set of curved washers.

19. The test device of claim 10 in which distinct predetermined pressure loads are obtained by a laminate of a corresponding multiple arrangement of individual curved washers all of which are provided with the same spring characteristic.

* * * * *